United States Patent [19]

Roth

[11] Patent Number: 5,395,850

[45] Date of Patent: Mar. 7, 1995

[54] 6,7-EPOXY PACLITAXELS

[75] Inventor: Gregory Roth, Cheshire, Conn.

[73] Assignee: Bristol-Myers Squibb Company, New York, N.Y.

[21] Appl. No.: 212,468

[22] Filed: Mar. 10, 1994

[51] Int. Cl.$^6$ .................. A61K 31/335; A61K 31/38; A61K 31/34; C07D 305/00
[52] U.S. Cl. .................. 514/471; 514/444; 514/475; 549/60; 549/493; 549/510; 549/511
[58] Field of Search ............... 549/510, 511, 60, 493; 514/444, 471, 475

[56] References Cited

U.S. PATENT DOCUMENTS 5,227,400  7/1993  Halton et al. .................. 514/444
5,254,580  10/1993  Chen et al. .................... 549/511

*Primary Examiner*—Joseph E. Evans
*Attorney, Agent, or Firm*—William T. Han

[57] ABSTRACT

The present invention provides paclitaxel derivatives of formula I

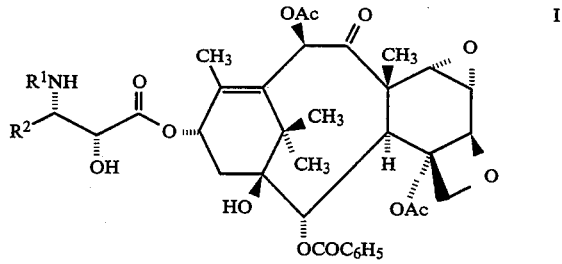

in which $R^1$ is —$COR^z$, in which $R^z$ is $RR^oN$—, $RHN$—, $RO$— or $R$;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

Also provided by this invention are pharmaceutical formulations (compositions) and a method of treating mammalian tumors with a compound of formula I.

9 Claims, No Drawings

6,7-EPOXY PACLITAXELS

FIELD OF INVENTION

The present invention provides compounds having antitumor activities.

BACKGROUND OF INVENTION

TAXOL® (paclitaxel) was first isolated from the stem bark of Western Yew, *Taxus brevifolia* Nut. (Taxaceae) and has the following structure (with the (C)2'-, 6-, 7-, and 13th-positions indicated):

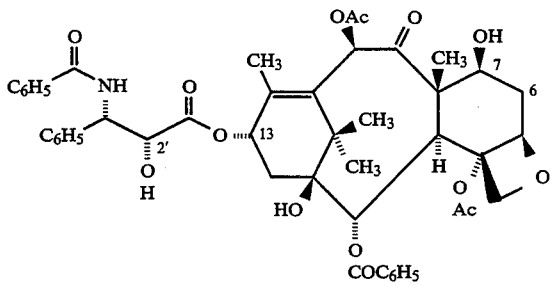

It was recently approved for the treatment of ovarian cancer; and studies involving breast, colon, and lung cancers have shown promising results.

Paclitaxel is unique among antimitotic drugs in that it promotes the assembly of stable microtubules from tubulin even under otherwise unfavorable conditions. The drug binds to microtubules, stabilizing them from depolymerization, thus disrupting the tubulin-microtubule equilibrium and consequently inhibiting mitosis. The mechanism of action, toxicology, clinical efficacy, etc. of paclitaxel are reviewed in a number of articles, such as in the article by Rowinsky et al. in Taxol: A Novel Investigational Antimicrotubule Agent, *J. Natl. Cancer Inst.*, 82: pp 1247–1259 (1990); and in "The Clinical Pharmacology and Use of Antimicrotubule Agents in Cancer Chemotherapeutics" *Pharmac. Ther.*, 52:35–84 (1991).

Since the discovery of its significant effectiveness in cancer treatment, many laboratories have launched programs to design paclitaxel analogues in search of better pharmacological profiles. Out of such programs, for example, was the discovery of Taxotere® of the formula

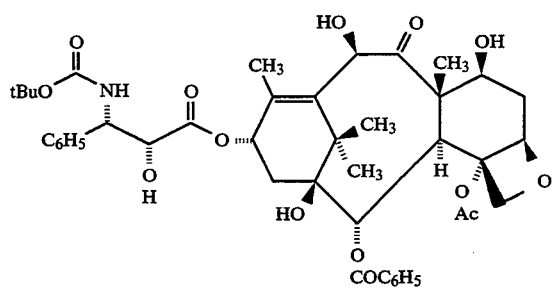

See, Biologically Active Taxol Analogues with Deleted A-Ring Side Chain Substitutents and Variable C-2' Configurations, *J. Med. Chem.*, 34, pp 1176–1184 (1991); Relationships between the Structure of Taxol Analogues and Their Antimitotic Activity, *J. Med. Chem.*, 34, pp 992–998 (1991).

The present invention relates to structurally novel paclitaxel derivatives with antitumor activities.

SUMMARY OF INVENTION

The present invention provides paclitaxel derivatives of formula I

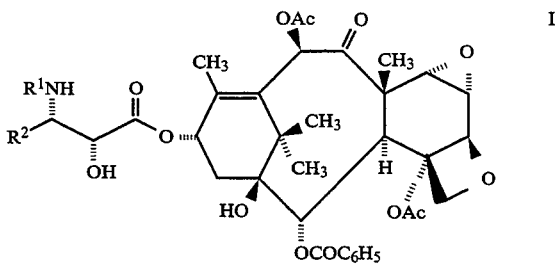

in which $R^1$ is $—COR^z$, in which $R^z$ is $RR^oN—$, $RHN—$, $RO—$ or $R$;

$R^2$ is $C_{1-6}$ alkyl, $C_{2-6}$ alkenyl, $C_{2-6}$ alkynyl, $C_{3-6}$ cycloalkyl, or a radical of the formula $—W—R^x$ in which W is a bond, $C_{2-6}$ alkenediyl, or $—(CH_2)_t—$, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or $—CF_3$ groups;

R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or $—CF_3$ groups.

Also provided by this invention are pharmaceutical formulations (compositions) and a method of treating mammalian tumors with a compound of formula I.

DETAILED DESCRIPTION OF INVENTION

The present invention provides paclitaxel derivatives of formula I

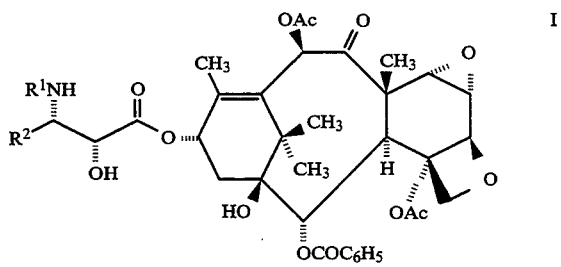

in which $R^1$ is $—COR^z$, in which $R^z$ is $RR^oN—$, $RHN—$, $RO—$ or $R$;

$R^2$ is $C_{1-6}$ alkyl, $C_{2-6}$ alkenyl, $C_{2-6}$ alkynyl, $C_{3-6}$ cycloalkyl, or a radical of the formula $—W—R^x$ in which W is a bond, $C_{2-6}$ alkenediyl, or $—(CH_2)_t—$, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or $—CF_3$ groups;

R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or $—CF_3$ groups.

In the instant application, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl, or the like groups; $C_{3-6}$ cycloalkyl refers to cyclopropyl, cyclobutyl, cyclopentyl, or cyclohexyl; $C_{2-6}$ alkynyl refers to straight or branched alkynyl groups such as ethynyl, propargyl (2-propynyl), 1-propynyl, 2-butynyl, 3-butynyl, 1-hexynyl, 4-methyl-2-pentynyl, and the like groups; $C_{2-6}$ alkenediyl refers to groups such as ethylene-1,2-diyl (vinylene), 2-methyl-2-butene-1,4-diyl, 2-hexene-1,6-diyl, and the like groups; $C_{1-6}$ alkyloxy (alkoxy) refers to straight or branched alkyloxy groups such as methoxy, ethoxy, n-propoxy, i-propoxy, n-butoxy, t-butoxy (t-butyloxy), n-pentyloxy, n-hexyloxy, or 3-methylpentyloxy, to name a few; heteroaryl refers to a five-membered aromatic ring containing at least one heteroatom selected from sulfur, oxygen or nitrogen, but up to 1 sulfur, 1 oxygen or 4 nitrogen atoms; heteroaryl also refers to a six-membered aromatic ring containing from 1 to 4 nitrogen atoms; and halogen refers to fluorine, chlorine, bromine, or iodine. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings. Azetidinone refers to azetidin-2-one. In the instant application all symbols once defined retain the same meaning until they are redefined.

The synthesis of a compound of formula I can be accomplished by a wide variety of methods. The synthetic methods, descriptions and specific examples that follow are only intended for the purpose of illustration, and are not to be construed as limiting in any manner ways to make compounds of the present invention by any other methods. The methods disclosed herein can be readily modified and/or adapted to make additional compounds of formula I not specifically disclosed.

In one embodiment, compound of formula Ia can be made by a process of Scheme I. In Step (a) of the Scheme, when compound of formula IIa is treated with DAST, compound of formula IIIa can be obtained. The DAST reaction can be conducted in a wide variety of solvents, including methylene chloride, tetrahydrofuran (THF), diethyl ether, toluene, and any combination thereof. In addition to compound IIIa, compounds of formula IVa and Va may be obtained as side products in the DAST reaction. It has been observed that the highest ratio of compound IIIa to compound IVa or Va is obtained when the reaction is run in a mixture of THF and toluene. In Step (b), compound IIIa is treated with dimethyldioxirane to afford epoxide of formula VIa. The oxidation with dimethyldioxirane can be conducted in a variety of solvents such as dichloromethane, 1,2-dichloroethane, tetrahydrofuran, methanol, ethyl acetate, acetic acid, methyl ethyl ketone, or a mixture of any of the aforementioned with acetone. The most desirable condition is in acetone at a temperature between $-20°$ C. to $5°$ C. Upon removal of Cbz group from compound of formula VIa in Step (c), compound of formula Ia is obtained.

In a more general embodiment of Scheme II, when compound of formula Ia is treated with an ester reducing agent such as tetrabutylammonium borohydride in Step (a), C-13 side chain is reductively cleaved to afford compound of formula VIIIa. In Step (b), azetidinone VII, in which $R^3$ is a hydroxy protecting group, is reacted with compound VIIIa to afford a compound of formula VI. Reactions analogous to Step (b) are well known, and Step (b) can be carried out in substantially the same manner as described in European Patent Applications 0,400,971 A2, 0,534,709 A1, 0,534,708 A1, and 0,534,707 A1; Tetrahedron, 48, No. 34, pp 6985–7012 (1992); Bioorganic and Medicinal Chemistry Letters, 3, No. 11, pp 2467–2470, pp 2479–2482 (1993); and Tetrahedron Letters, 34, No. 26, pp 4149–4152 (1993). These references describe the reaction of class of azetidinones of formula VII with (C)13-hydroxy group of baccatin III derivatives or metal alkoxide thereof to afford paclitaxel analogues with a variety of (C)13-side chains.

For example, the coupling reaction between a taxane of formula VIIIa and an azetidinone of formula VII is conducted in an inert organic solvent such as tetrahydrofuran at reduced temperature in the range of about $0°$ C. to about $-78°$ C. The azetidinones of formula VII may be used as a racemic mixture; in such case, the azetidinone reactant is preferably used in at least 2 equivalents relative to the taxane reactant, and more preferably from about 3 to about 6 equivalents. Chiral azetidinones may also be used, and in such case one equivalent of the azetidinone relative to the taxane may be sufficient, but preferably the azetidinone is used in slight excess, for example up to 1.5 equivalents.

Furthermore, for Step (b) of Scheme II, it is advantageous to convert the hydroxy group on the (C)13-carbon into a metal alkoxide before the coupling. The metal cation of said metal alkoxide is preferably selected from Group Ia or IIa metals. The formation of a desired metal alkoxide may be done by reacting a compound of formula VIIIa with a strong metal base, such as lithium diisopropylamide, $C_{1-6}$ alkyllithium, lithium bis(trimethylsilyl)amide, phenyllithium, sodium hydride, potassium hydride, lithium hydride, or the like base. For example when lithium alkoxide is desired, a compound of formula VIIIa may be reacted with n-butyllithium in an inert solvent such as tetrahydrofuran.

The general class of azetidinones of formula VII are also well known. Their syntheses or syntheses of their precursors have been reported such as by Holton in European Patent Application 0,400,971 A2 published on Dec. 5, 1990; by Holton in European Patent Applications 0,534,709 A1, 0,534,708 A1, and 0,534,707 A1, all three published on Mar. 31, 1993; also by Holton in PCT application WO 93/06079 published on Apr. 1, 1993; and in Bioorganic and Medicinal Chemistry Letters, 3, No. 11, pp 2475–2478 (1993); by Ojima et al. in Tetrahedron, 48, No. 34, pp 6985–7012 (1992); Journal of Organic Chemistry, 56, pp 1681–1683 (1991); Bioorganic and Medicinal Chemistry Letters, 3, No. 11, pp 2479–2482 (1993); and Tetrahedron Letters, 33, No. 39, pp 5737–5740 (1992); by Brieva et al. in J. Org. Chem., 58, pp 1068–1075; by Palomo et al. in Tetrahedron Letters, 31, No. 44, pp 6429–6432 (1990); by Gunda I. Georg et al in Bioorganic and Medicinal Chemistry Letters, 3, No. 11, pp 2467–2470 (1993); European Application 552,041 published on Jul. 21, 1993; and in our copending U.S. application Ser. No. 092,170 filed on Jul. 14, 1993: all aforementioned disclosures are herein incorporated by reference in their entirety. The methods that can be easily adapted to variations in order to produce other azetidinones within the scope of formula VII, but not specifically disclosed herein or in the above references or reported elsewhere, will be obvious to anyone skilled in the art.

Upon removal of hydroxy protecting group $R^3$ in Step (c), a compound of formula I can be obtained. As used herein, hydroxy protecting groups are moieties which can be employed to block or protect the hydroxy function and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 2,2,2-trichloroethyoxymethyl, 2,2,2-trichloroethyloxycarbonyl, tetrahydropyranyl, tetrahydrofuranyl, t-butyl, benzyl, p-nitrobenzyl, p-methoxybenzyl, diphenylmethyl, tri$C_{1-6}$alkylsilyl, triphenylsilyl, 1-ethoxyethyl, and the like. Preferred protecting groups for the 2'-hydroxy group of paclitaxel and a derivative thereof are 1-ethoxyethyl, triethylsilyl, 2,2,2-trichloroethyloxycarbonyl and benzyloxycarbonyl; even more preferred group is benzyloxycarbonyl, which can be removed conveniently by catalytic hydrogenolysis. Other suitable protecting groups which can be used are found in Chapter 2 of "Protecting Groups in Organic Synthesis", Second Ed., by Theodora W. Greene and Peter G. M. Wuts (1991, John Wiley & Sons); the disclosure thereof is herein incorporated by reference.

SCHEME I

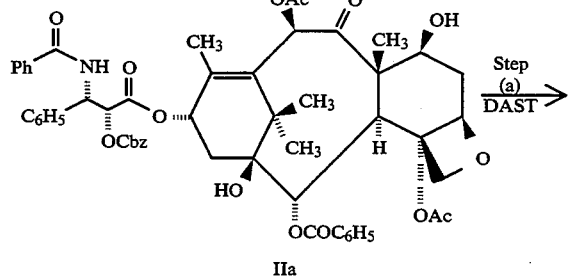

IIa

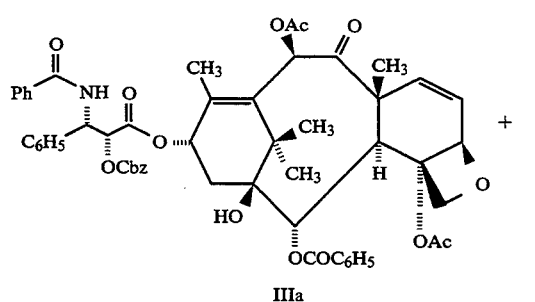

IIIa

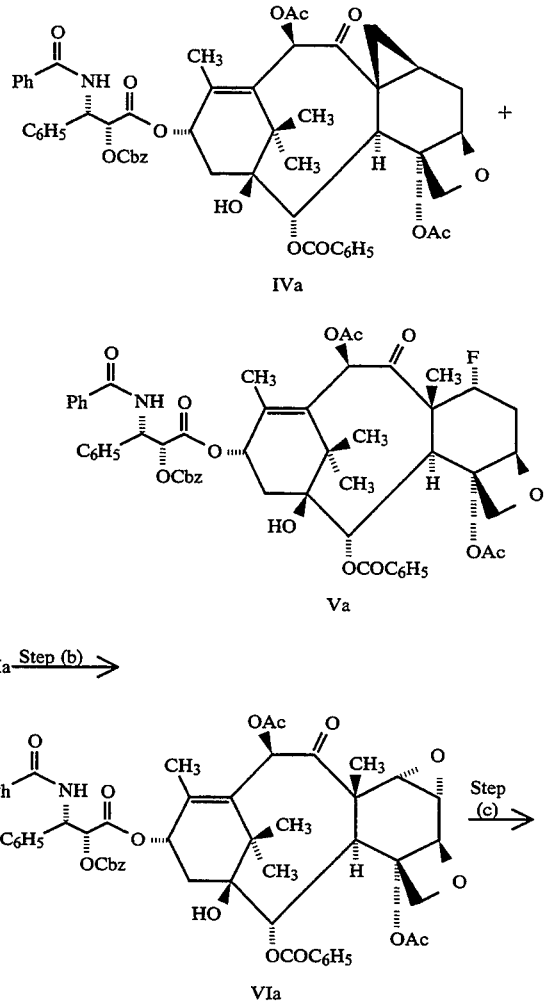

IVa

Va

IIIa —Step (b)→

VIa —Step (c)→

Ia

SCHEME II

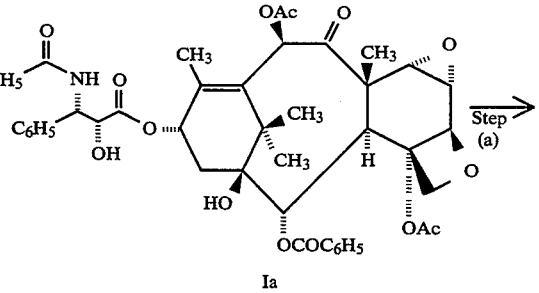

Ia —Step (a)→

-continued
SCHEME II

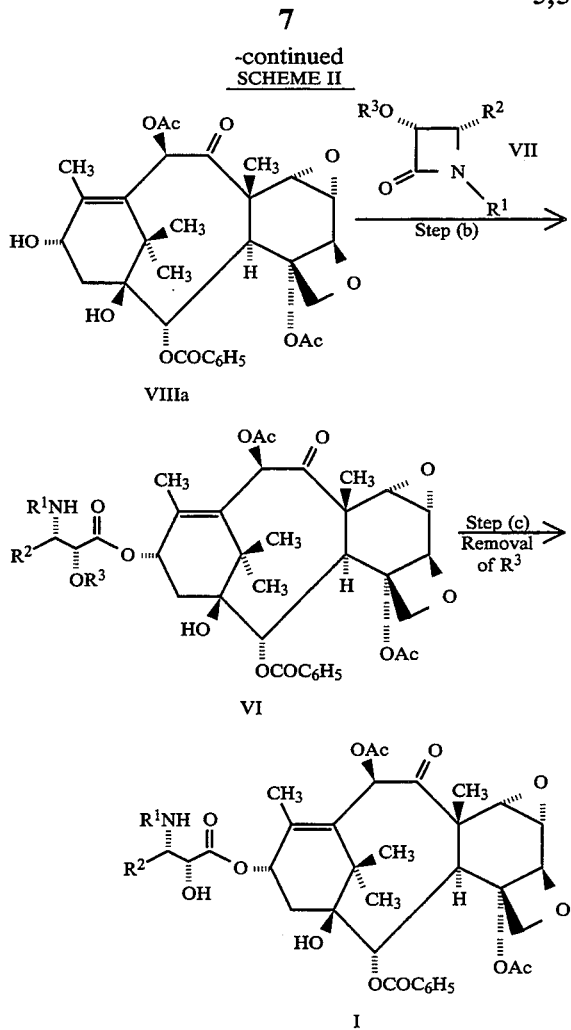

DESCRIPTION OF SPECIFIC EMBODIMENTS

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dr), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are:

CAN: ceric ammonium nitrate
MS: mass spectrometry
HRMS: high resolution mass spectrometry
DAST: diethylaminosulfur trifluoride
Ac: acetyl
Ph: phenyl
Ar: aryl
DCI: desorption chemical ionization
Y: yield
v/v: volume/volume
FAB: fast atom bombardment
NOBA: m-nitrobenzylalcohol
min: minute(s)
h: hour(s)
tBu: tertiarybutyl
Cbz: benzyloxycarbonyl
Bz: benzoyl
TES: triethylsilyl

EXAMPLE 1

2'-O-(Benzyloxycarbonyl)paclitaxel (IIa)

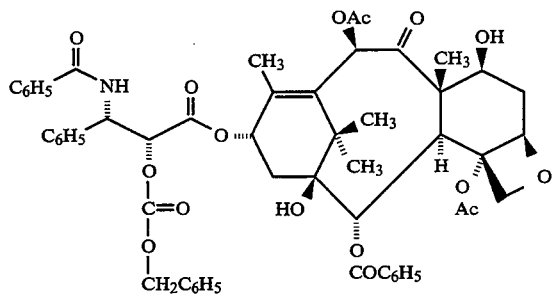

To a stirred, room temperature solution of paclitaxel (150 mg, 0.176 mmol) and N,N-diisopropylethylamine (93 µL, 0.534 mmol, 3 eq.) in anhydrous $CH_2Cl_2$ (4 mL) was added benzyl chloroformate (75 µL, 0.525 mmol, 3 eq.) at room temperature. The reaction mixture was stirred at room temperature for 3 h. The reaction mixture was concentrated to 2 mL in volume and the product was purified on a silica gel column, using 1:1 of EtOAc/hexanes as eluent, to obtain 150 mg (0.152 mmol, Y: 86%) of the title compound, IIa, as a white powder; mp, 140°–150° C. (decomposition); $[\alpha]_D^{20} -53.5°$ (c=0.2, 95% EtOH); $^1$H-NMR (300 MHz, acetone-$d_6$) $\delta$ ppm: 1.18 (3H, s, 17-H$_3$), 1.92 (3H, s, 16-H$_3$), 1.66 (3H, s, 19-H$_3$), 1.96 (3H, s, 18-H$_3$), 2.16 (3H, s, 10-OAc), 2.5 (3H, s, 4-OAc), 3.53 (1H, d, J=5.89 Hz, 7-OH, exchanged with $D_2O$), 3.85 (1H, d, J=7.19

Hz, 3-H), 3.9 (1H, s, 1-OH, exchanged with D$_2$O), 4.17 (2H, ABq, 20-H$_2$), 4.25 (1H, m, 7-H), 4.97 (1H, d, J=9.56 Hz, 5-H), 5.19 (2H, ABq, OCH$_2$C$_6$H$_5$), 5.54 (1H, d, J=5.5 Hz, 2'-H), 5.68 (1H, d, J=7.13 Hz, 2-H), 6.01 (1H, dd, J=5.5, 9.05 Hz, 3'-H), 6.17 (1H, bt, J=9.0 Hz, 13-H), 6.42 (1H, s, 10-H), 7.28–7.69 (16H, m), 7.87 (2H, "d", J=8 Hz, 3'-NHCOPh), 8.14 (2H, "d", J=8 Hz, 2-CO$_2$Ph), 8.55 (1H, d, J=9.06 Hz, NH, exchanged with D$_2$O); MS (FAB-NOBA/NaI+KI) m/e: 988 (M+H)$^+$, 1010 (M+Na)$^+$, 1026 (M+K)$^+$; IR (KBr) $\nu$ max: 3448, 1748 (C=O), 1726 (CONH), 1250 (C—O) cm$^{-1}$; UV (MeOH:H$_2$O, 1:1) $\lambda$ max: 198 ($\epsilon$ 7.3×10$^4$), 230 nm ($\epsilon$ 2.7×10$^4$); HRMS calcd for C$_{55}$H$_{58}$NO$_{16}$ (MH$^+$): 988.3756, found: 988.3766.

Anal. calcd for C$_{55}$H$_{57}$NO$_{16}$·H$_2$O: C, 65.67; H, 5.92; N, 1.40. Found: C, 65.99; H, 5.64; N, 1.33.

EXAMPLE 2

2'-O-Benzyloxycarbonyl-6,7-dehydropaclitaxel (IIIa)

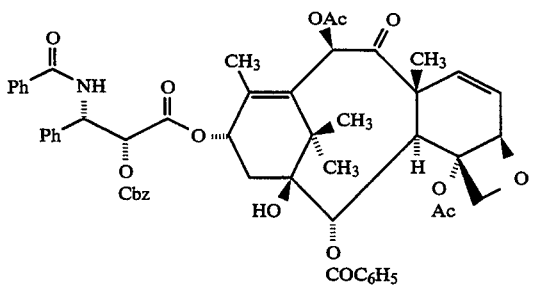

2'-O-(Benzyloxycarbonyl)paclitaxel (IIa) (514 mg, 0.521 mmol) was dissolved in THF (3 mL) and Et$_2$O (6 mL). This solution was cooled to −78° C. and DAST (0.134 mL, 1.040 mmol) was added dropwise. The reaction was stirred at −78° C. for 3 h, and then left at room temperature overnight. When the reaction was complete, the solvent was partially removed in vacuo, and the residue was chromatographed with 30–40% EtOAc in hexane to afford 73 mg (Y: 14.5%) of the desired product; $^1$H-NMR (CDCl$_3$, 300 MHz) $\delta$ ppm: 8.15 (d, J=7.1 Hz, 2H), 7.71 (d, J=7.1 Hz, 2H) 7.63- 7.24 (m, 16H) 6.90 (d, exch, J=9.3 Hz, 1H) 6.25 (bt, 1H) 6.21 (s, 1H) 6.05 (dd, J$_1$=9.9 Hz, J$_2$=5.6 Hz, 1H) 5.96 (dd, J$_1$=9.9 Hz, J$_2$=2.7 Hz, 1H) 5.86 - 5.82 (m, 2H) 5.42 (d, J=2.5 Hz, 1H) 5.18- 5.09 (m, 3H) 4.37 (AB q, J=8.2 Hz, 2H) 4.00 (d, J=6.6 Hz, 1H) 2.48-1.12 (m, 21H, including s at 2.44, 3H; 2.18, 3H; 1.86, 3H; 1.84, 3H; 1.23 3H; 1.13, 3H); $^{13}$C-NMR (CDCl$_3$, 75 MHz) $\delta$ ppm: 205.5, 169.5, 169.1, 167.8, 167.1, 167.0, 154.1, 141.9, 139.9, 136.8, 134.3, 133.7, 133.5, 132.0, 130.2, 129.2, 129.1, 128.9, 128.7, 128.4, 127.2, 126.6, 126.2, 81.2, 81.1, 78.8, 76.9, 76.3, 75.9, 75.7, 71.9, 70.7, 55.4, 52.7, 43.1, 41.4, 35.8, 26.4, 22.8, 22.1, 21.0, 20.8, 20.5, 14.5.

Alternate Run 2'-O-(Benzyloxycarbonyl)paclitaxel (IIa) (2.0 g, 2.04 mmol) was dissolved in toluene/THF (4:1, 50 mL) and cooled to −78° C. under an inert atmosphere. To this was added DAST (0.69 mL, 5.1 mmol) and the resulting solution was allowed to gradually warm to ambient temperature over a 16 h period. The solution was quenched with saturated aqueous sodium bicarbonate and diluted with ethyl acetate. The organic fraction was then dried (MgSO$_4$) and concentrated to furnish a crude mixture. The desired product was isolated by chromatography (silica gel, 10% acetonitrile in dichloromethane) to furnish the title product as a white solid (410 mg, yield 21%).

EXAMPLE 3

2'-O-Benzyloxycarbonyll-6,7-$\alpha$-epoxypaclitaxel (VIa)

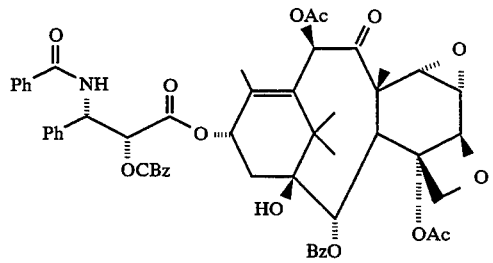

A solution of compound IIIa (200 mg, 0.2 mmol) in acetone (1 mL) was cooled to −20° and treated with a 0.14M acetone solution of freshly prepared dimethyldioxirane (5 mL, 0.7 mmol). The resulting solution was placed in a freezer (−20° C.) and allowed to stand overnight. The solution was then evaporated. ($^1$H-NMR indicated that the reaction proceeded to give 30% of the desired product.) The crude material was then treated with additional dimethyldioxirane, as described above, until $^1$H-NMR indicated completion of the reaction. Evaporation of the solvent furnished the desired epoxide as a white solid (200 mg, 100%); $^1$H-NMR (300 MHz, CDCl$_3$): $\delta$ 8.09 (d, 2H, J=21.0 Hz), 7.70 (d, 2H, J=21.0 Hz), 7.58-7.23 (complex m, 16H), 6.93 (d, 1H, J=12.0 Hz), 6.45 (s, 1H), 6.27-6.21 (m, 1H), 5.98 (dd, 1H, J=2.3, 9.4 Hz), 5.83 (d, 1H, J=9.6 Hz), 5.47-5.43 (m, 2H), 5.14-5.09 (m, 2H), 4.41 (ABq, 2H, J-9.0, 105.0 Hz), 3.95 (d, 1H, J=6.0 Hz), 3.24 (t, 1H, J=3.0 Hz), 3.01 (d, 1H, J=3.0 Hz), 2.64-2.56 (m, 1H), 2.52 (s, 3H), 2.65-2.17 (m, 4H, including singlet at 2.23), 1.98 (s, 3H), 1.88-1.72 (m, 4H, including singlet at 1.86), 1.22 (s, 3H), 1.13 (s, 3H); $^{13}$C-NMR (75.6 MHz, CDCl$_3$): $\delta$ 204.6, 169.3, 168.2, 167.9, 167.2, 166.7, 154.0, 142.1, 136.7, 134.3, 133.7, 133.5, 133.0, 132.0, 130.2, 129.9, 129.0, 128.8, 128.7, 128.5, 128.4, 128.3, 128.2, 128.1, 127.1, 126.5, 81.6, 81.2, 81.0, 78.7, 78.2, 76.6, 76.5, 75.9, 75.7, 74.7, 71.9, 70.7, 66.9, 59.9, 53.4, 52.6, 51.1, 43.2, 38.9, 35.3, 26.1, 22.9, 22.8, 22.0, 21.8, 20.7, 20.4, 15.4, 14.6, 14.4.

EXAMPLE 4

6,7-$\alpha$-Epoxypaclitaxel (Ia)

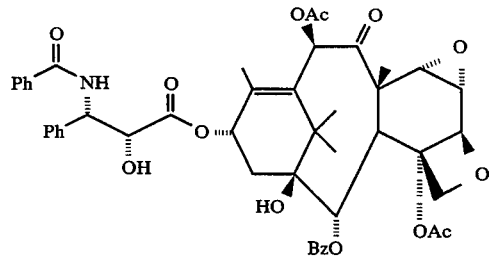

A solution of compound VIa (190 mg, 0.19 mmol) in ethyl acetate (4 mL) was flushed with argon in a Parr bottle and treated with palladium on carbon (12.0 mg). The resulting suspension was shaken under 50 psi of hydrogen for 3 h then was vented and filtered through a plug of celite. The filtrate was then evaporated and the residue was purified by silica gel chromatography (hexanes/ethyl acetate 1:1) to furnish the desired product as a white solid (126.6 mg, 77.6%). m.p. 186°–187° C.; $^1$H-NMR (300 MHz, CDCl$_3$): δ 8.07 (d, 2H, J=9.0 Hz), 7.79-7.73 (m, 2H), 7.61-7.25 (complex m, 11H), 7.15 (d, 1H, 12.0 Hz), 6.42 (s, 1H), 6.19-6.16 (m, 1H), 5.82 (dd, 1H, J=2.2, 9.3 Hz), 5.73 (d, 1H, J=6.0 Hz), 5.34 (d, 1H, J=3 Hz), 4.80-4.78 (m, 1H), 4.36 (ABq, 2H, J=9.0, 65.0 Hz), 4.02 (d, 1H, J=6.0 Hz), 3.79 (d, 1H, J=3.0 Hz), 3.25 (t, 1H, J=3.0 Hz), 3.01 (d, 1H, J=3.0 Hz), 2.39-2.33 (m, 5H), 2.22 (s, 3H), 1.87 (s, 3H), 1.80-1.66 (m, 5 H), 1.24-1.14 (m, 5H); $^{13}$C-NMR (75.6 MHz, CDCl$_3$): δ 204.2, 172.0, 169.0, 141.4, 138.1, 133.8, 133.4, 131.9, 129.9, 128.9, 128.8, 128.7, 128.2, 127.1, 127.0, 81.8, 78.9, 78.0, 77.4, 74.5, 73.3, 71.8, 59.6, 54.6, 53.8, 51.2, 43.0, 38.8, 35.5, 26.1, 22.8, 21.2, 20.7, 15.3, 14.7.

EXAMPLE 5

6,7-α-Epoxy Baccatin III (VIIIa)

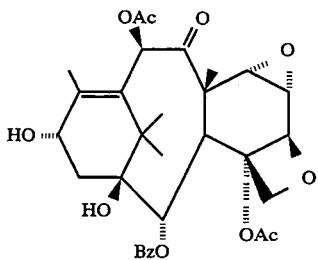

A solution of 6,7-α-epoxypaclitaxel (99 mg, 0.1 mmol) in dichloromethane/2% methanol (6 mL) was treated with tetrabutylammonium borohydride (59.7 mg, 0.2 mmol) and the resulting solution was allowed to stir at ambient temperature for 5 h. The reaction was quenched by addition of saturated aqueous ammonium chloride (2 mL) and the organic fraction was dried (MgSO$_4$) and concentrated. The crude product was chromatographed on silica gel (eluted with 10% CH$_3$CN in CH$_2$Cl$_2$) to furnish the desired product as a white foam (44.7 mg, 66%); $^1$H-NMR (300 MHz, CDCl$_3$): δ 8.07-8.04 (m, 2H), 7.63-7.5 (m, 1H), 7.50-7.44 (m, 2H), 6.44 (s, 1H), 5.68 (d, 1H, J=6.0 Hz), 5.32 (d, 1 H, J=2.7 Hz), 4.82 (broad q, 1H, J=6.0, 15.0 Hz), 4.34 (ABq, 2H, J=9.0, 63.0 Hz), 4.14 (d, 1H, J=6.0 Hz), 3.45 (s, 1H), 3.24 (t, 1H, J=3.0 Hz), 3.00 (d, 1H, J=3.0 Hz), 2.33-2.14 (m, 7H, including singlets at 2.28, 2.22), 2.10 (s, 3H), 1.84-1.69 (m, 5H including singlets at 1.84, 1.72), 1.09 (s, 6H); $^{13}$C-NMR (75.6 MHz, CDCl$_3$): δ 204.6, 170.0, 169.4, 166.7, 145.9, 133.7, 132.0, 130.0, 129.9, 129.1, 128.6, 82.0, 78.9, 78.1, 77.4, 77.3, 74.5, 68.0, 59.6, 53.4, 51.2, 42.7, 39.0, 38.7, 26.0, 22.8, 20.8, 15.2, 14.9.

EXAMPLE 6

3′-N-Debenzoyl-N-t-butoxycarbonyl-3′-desphenyl-3′-(2-furyl)-6,7-α-epoxypaclitaxel (Ib)

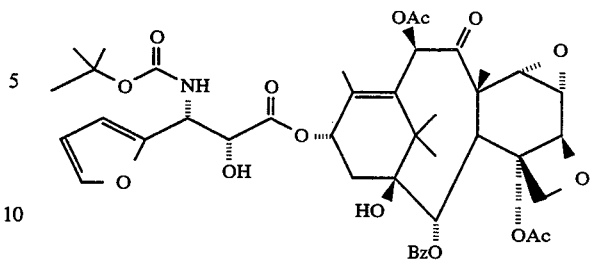

A solution of compound VIIIa (475.0 mg, 0.81 mmol) in dry THF (15 mL) was cooled to −55° C. under an inert atmosphere and treated with a solution of lithium hexamethyldisilazane (1M in THF, 0.97 mL, 0.97 mmol). The resulting solution was allowed to stir for 5 min, then a THF solution (3 mL) of (3R,4R)-3-triethylsilyloxy-4-(2-furyl)-N-t-butoxycarbonylazetidin-2-one (295.0 mg, 0.81 mmol) was added over 5 min. The resulting solution was allowed to stir at −55° C. for 10 min then the reaction was warmed to 0° C. and allowed to stir for 30 min. The reaction was then quenched by addition of saturated NH$_4$Cl solution, transferred to a separatory funnel and extracted with ethyl acetate. The organic fraction was dried (MgSO$_4$) and concentrated to give 2′-O-triethylsilyl protected taxane as a white foam.

This crude product was then dissolved in acetonitrile (6 mL) and cooled to 0° C. in an ice bath. To this solution was added an aqueous solution of HCl (1M, 2.4 mL, 2.4 mmol). The resulting solution was allowed to stir at that temperature for 1.5 h then was quenched with saturated aqueous NaHCO$_3$ and extracted with ethyl acetate. The organic fraction was then dried (MgSO$_4$) and concentrated to give the product as a white foam. The crude product was purified by silica gel chromatography (eluted with hexanes/ethyl acetate 1:1) to furnish 467.6 mg (74% overall) of compound Ib as a white foam.

The entire reaction can be repeated with racemic form of lactam VIIa. In such case 4–5 equivalents of lactam VIIa is used for 100% diastereoselection to afford the desired isomer Ib; $^1$H-NMR (300 MHz, CDCl$_3$): δ 8.06 (d, 2H, J=9.0 Hz), 7.61 (t, 1H, J=6.0 Hz), 7.48 (t, 2H, J=9.0 Hz), 7.41 (s, 1H), 6.47 (s, 1H), 6.38-6.36 (m, 1H)), 6.32-6.31 (m, 1H), 6.20-6.17 (m, 1H), 5.75 (d, 1H, J=6.0 Hz), 5.39-5.25 (m, 3H), 4.38 (ABq, 2H, J=6.0, 81.0 Hz), 4.02 (d, 1H, J=6.0 Hz), 3.26 (t, 1H, J=3.0 Hz), 3.03 (d, 1H, J=3.8 Hz), 2.47-1.16 (complex m, 32H, including singlets at 2.33, 2.21, 1.99, 1.93, 1.87, 1.38, 1.25); $^{13}$C-NMR (75.6 MHz, CDCl$_3$): δ 204.2, 169.3, 168.6, 166.7, 155.2, 151.4, 149.6, 142.3, 141.1, 136.0, 133.7, 133.2, 129.9, 129.0, 128.6, 110.6, 107.3, 81.8, 80.3, 78.6, 78.1, 74.6, 72.2, 71.7, 59.7, 53.6, 51.7, 51.1, 43.1, 38.8, 35.2, 29.6, 28.1, 25.9, 22.7, 21.5, 20.7, 15.3, 14.7.

EXAMPLE 7

3′-Desphenyl-3′-(2-furyl)-6,7-α-epoxypaclitaxel (Ic)

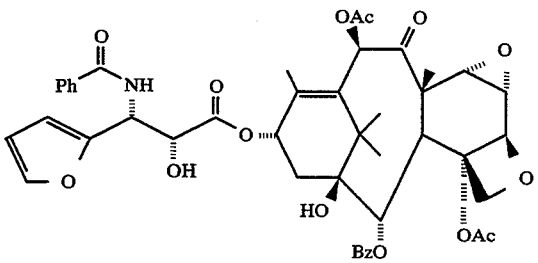

The title compound was prepared in an identical manner to compound Ib of Example 6 by using 5–6 equivalents of (±)-cis-3-triethylsilyloxy-4-(2-furyl)-N-benzoylazetidin-2-one. The desired product was isolated as a white foam; $^1$H-NMR (300 MHz, CDCl$_3$): δ 8.05 (d, 2H, J=7.6 Hz), 7.74 (d, 2H, J=7.2 Hz), 7.60 (t, 1H, J=7.2 Hz), 7.52-7.38 (m, 5H), 6.93 (d, 1H, J=9.3 Hz), 6.43 (s, 1H), 6.37 (s, 2H), 6.18 (t, 1H, J=8.2 Hz ), 5.88 (dd, 1H, J=2.2, 9.3 Hz), 5.73 (d, 1H, J=6.0 Hz), 5.36 (d, 1H, J=3.0 Hz), 4.81 (bs, 1H), 4.49 (d, 1H, J=8.0 Hz), 4.24 (d, 1H, J=8.0 Hz), 4.01 (d, 1H, J=6.0 Hz), 3.65 (bs, 1H), 3.25 (t, 1H, J=3.0 Hz), 3.01 (d, 1H, J=4.0 Hz), 2.50-2.30 (m, 6H), 2.21 (s, 3H), 1.87-1.86 (m, 6 H), 1.21 (s, 3H), 1.13 (s, 3H); $^{13}$C-NMR (75.6 MHz, CDCl$_3$): δ 204.3, 171.9, 169.3, 168.9, 166.9, 166.7, 150.9, 142.6, 141.4, 133.8, 133.5, 132.0, 130.0, 129.0, 128.7, 127.0, 110.7, 107.9, 81.8, 78.8, 78.1, 76.5, 74.5, 72.0, 71.7, 59.7, 53.7, 51.2, 50.3, 43.1, 38.8, 35.4, 26.1, 22.7, 21.3, 20.7, 15.3, 14.7.

EXAMPLE 8

3'-N-Debenzoyl-N-t-butoxycarbonyl-3'-desphenyl-3'-isobutenyl-6,7-α-epoxypaclitaxel (Id)

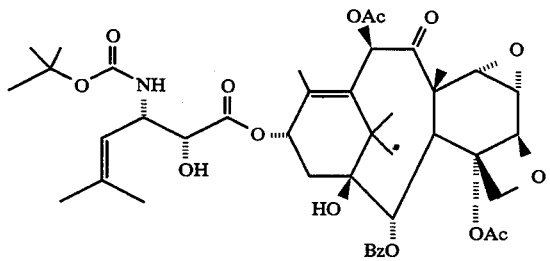

The title compound was prepared in an identical manner to compound Ib of Example 6 by using 5–6 equivalents of racemic lactam VIIc. The desired product was isolated as a white foam; $^1$H-NMR (300 MHz, CDCl$_3$): δ 8.07-8.04 (m, 2H), 7.64-7.59 (m, 1H), 7.47 (t, 2H, J=9.0 Hz), 6.47 (s, 1H), 6.13 (t, 1H, J=9.0 Hz), 5.74 (d, 1H, J=6.0 Hz), 5.38 (d, 1H, J=6.0 Hz), 5.28 (d, 1H, J=9.0 Hz), 4.87-4.49 (m, 3H), 4.50 (d, 1H, J=9.0 Hz), 4.26-4.23 (m, 2H), 4.03 (d, 1H, J=6.0 Hz), 3.45 (t, 1H, J=3.0 Hz), 3.03 (d, 1H, J=3.8 Hz), 2.40-1.16 (complex m, 35 H, including singlets at 2.38, 2.23, 1.87, 1.83, 1.75, 1.37, 1.24, 1.16); $^{13}$C-NMR (75.6 MHz, CDCl$_3$): δ 204.4, 169.35, 168.64, 166.71, 142.0, 137.9, 136.0, 133.8, 133.1, 129.9, 129.0, 128.6, 120.7, 81.82, 79.8, 78.6, 78.2, 76.7, 76.5, 74.6, 73.8, 71.8, 60.7, 59.7, 53.7, 51.4, 51.2, 44.6, 43.1, 38.8, 35.4, 28.2, 28.0, 25.8, 25.7, 24.8, 24.3, 22.6, 21.4, 21.2, 18.6, 15.3, 15.8.

EXAMPLE 9

Preparation of hydrobenzamide, PhCH(—N=CHPh)2

To a 3 L 3-necked flask equipped with a mechanical stirrer and a thermometer was added 1 L of concentrated NH$_4$OH (ca 30%) (14.8 moles). A solution of benzaldehyde (265 g, 2.50 mol) in 500 mL of 2-propanol was added in one portion. The mixture was stirred vigorously at ca 22° C. for 43 hours. The resulting slurry was filtered and the filter cake was washed with water (1 L). After drying in vacuo, 242.4 g of hydrobenzamide was obtained as a white solid (mp 100°–102° C.) for a 97.4% yield.

The above procedure can be followed to prepare bis-imines of the general formula R$^2$CH(—N=CHR$^2$)$_2$: i.e. hydrofuramide (R$^2$=2-furyl) hydrothienamide (R$^2$=2-thienyl)

EXAMPLE 10

(±)-cis-3-Acetyloxy-1-[(phenyl) (benzylidenimino)methyl]-4-phenylazetidn-2-one (IXa)

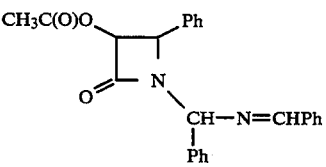

To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxyacetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous NH$_4$Cl (sat) (150 mL, 100 mL), aqueous NaHCO$_3$ (saturated) (120 mL) and brine (120 mL). For purposes of characterization, the title compound can be isolated at this stage by drying the organic phase over MgSO$_4$, filtering, and removing the solvent in vacuo. This provided the desired product in quantitative crude yield as a red glass.

HPLC purity (area): 87.9% (1:1 mixture of diastereomers); $^1$H-NMR (CDCl$_3$, 200 MHz): δ 8.45 (s, 1H, N=CH), 7.80–7.85 (m, 1H, Ph), 7.60–7.65 (m, 1H, Ph), 7.26–7.50 (m, 9H, Ph), 7.00–7.10 (m, 4H, Ph), 6.28 (s, 0.5H, NCHN), 6.23 (s, 0.5H, NCHN), 5.81 (d, J=4.8 Hz, 0.5 H, H-3), 5.76 (d, J=4.8 Hz, 0.5H, H-3), 5.30 (d, J=4.8 Hz, 0.5 H, H-4), 4.75 (d, J=4.8 Hz, 0.5 H, H-4), 1.63 (s, 3H, CH$_3$CO); IR (KBr): ν (cm$^{-1}$)=1763 (C=O), 1641 (C=N); UV (methanol): λ max (nm)=216, 252.

EXAMPLE 11

(±)-cis-3-Acetyloxy-4-phenylazetidin-2-one (Xa)

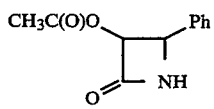

The solution of the compound of Example 10 in ethyl acetate (500 mL) from above was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite. The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine-HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous NaHCO3 (saturated) (300 mL) and brine (250 mL). The organic layer was dried over MgSO4, filtered and concentrated in vacuo to a final volume of 75 mL. This mixture was cooled to 4° C. and the precipitated product isolated by filtration. The filter cake was washed with hexane (200 mL) to provide 16.12 g (78.1% overall yield from hydrobenzamide) of the title compound as white needles.

mp=150°-151° C.; HPLC purity (area): 99.8%; $^1$H-NMR (CDCl3, 200 MHz): δ=7.30-7.38 (m, 5H, Ph), 6.54 (bs, exchangeable, 1H, NH), 5.87 (dd, J=2.7, 4.7 Hz, 1H, H-3), 5.04 (d, J=4.7 Hz, 1H, H-4), 1.67 (s, 3H, CH3CO); IR (KBr): ν (cm$^{-1}$)=3210 (N-H), 1755, 1720 (C=O); KF: 0.17%.

Anal. Calcd. for C11H11NO3: C, 64.38; H, 5.40; N, 6.83. Found: C, 64.07; H, 5.34; N, 6.77.

EXAMPLE 12

(±)-cis-3-Acetyloxy-1-[(2-furyl)(2-furylmethylenimino)methyl]-4-(2-furyl)azetidin-2-one (IXb)

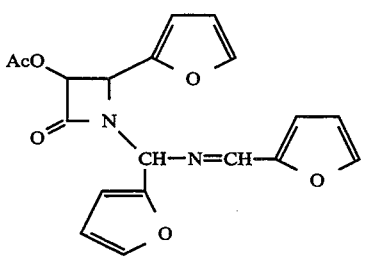

The title compound was prepared according to the procedure described in Example 10 except that hydrofuramide was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (Y: 90.4%) of the title compound as a pale red syrup.

Obtained as a 1:1 mixture of diastereomers; $^1$H-NMR (CDCl3; 200 MHz): δ 8.211 (s, 0.5H, N=CH), 8.208 (s, 0.5H, N=CH), 7.14–7.59 (m, 3H, furyl), 6.90 (d, J=3.5 Hz, 0.5H, furyl), 6.83 (d, J=3.5 Hz, 0.5H, furyl), 6.10–6.53 (m, 6H, furyl, NCHN), 5.90 (d, J=4.9 Hz, 0.5H, H-3), 5.86 (d, J=4.8 Hz, 0.5H, H-3), 5.35 (d, J=4.8 Hz, 0.5H, H-4), 4.90 (d, J=4.9 Hz, 0.5H, H-4), 1.91 (s, 1.5H, CH3CO),1.88 (s, 1.5H, CH3CO ); IR (film): ν (cm$^{-1}$)=1778, 1753 (C=O), 1642 (C=N); UV (methanol): λ max (nm)=220, 278.

EXAMPLE 13

(±)-cis-3-Acetyloxy-4-(2-furyl)azetidin-2-one (Xb)

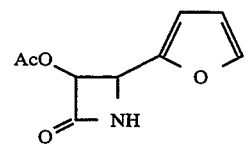

The title compound was prepared according to the procedure described in Example 11 except that the product was isolated by preparative TLC and the reaction was performed on the 2.7 mmol scale based on the original amount of hydrofuramide. Thus, the crude product of Example 12 (1.00 g) was re-dissolved in ethyl acetate (50 mL) and added to 10% palladium on activated charcoal (150 mg). Purification of the crude solid by preparative TLC (2 mm silica gel, eluted with 1:1 ethyl acetate/hexane) gave 386 mg (65.8% corrected overall yield from hydrofuramide) of the title compound as a yellow solid. This was recrystallized from ethyl acetate/hexane.

mp=118°-119° C.; HPLC purity (area): 99.4%; $^1$H-NMR (CDCl3, 200 MHz): δ 7.44 (t, J=1.3 Hz, 2H, furyl), 6.39 (d, J=1.3 Hz, 1H, furyl), 6.21 (bs, exchangeable, 1H, NH), 5.88 (dd, J=2.2, 4.6 Hz, 1H, H-3), 5.05 (d, J=4.6 Hz, 1H, H-4), 1.92 (s, 3H, CH3CO); IR (KBr): ν (cm$^{-1}$)=3203 (N-H), 1756, 1726 (C=O); UV (methanol): λ max (nm)=222.

EXAMPLE 14

(±)-cis-3-Acetyloxy-1-[(2-thienyl) (2-thienylmethylenimino)methyl]-4-(2-thienyl)azetidin-2-one (Ixc)

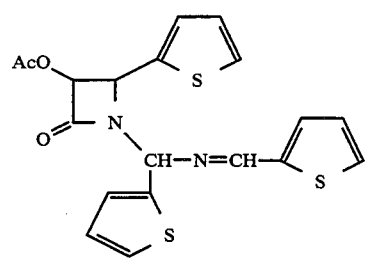

The title compound was prepared according to the procedure described in Example 10 except that hydrothienamide was used instead of hydrobenzamide. Thus, hydrothienamide (30 g, 94.7 mmol), thiethylamine (15.84 mL, 114 mmol) and acetoxyacetyl chloride (11.6 mL, 108 mmol) provided the title compound as viscous oil. The product obtained contained a mixture of diastereomers. $^1$H-NMR (CDCl3): δ 8.52 (s, 1H), 8.502 (s, 1H), 7.51 (d, J=4.9 Hz, 1H), 7.45 (d, J=4.4 Hz, 1H), 7.41 (d, J=3.1 Hz, 1H), 7.37 (d, 1H), 7.30 (m, 3H), 7.16 (m, 1H), 7.16 (m, 3H), 7.09 (m, 2H), 6.94 (m, 1H), 6.89 (m, 1H), 6.81-6.74 (m, 4H), 6.48 (s, 1H), 6.43 (s, 1H), 5.85 (m, 2H), 5.59 (d, J=4.8 Hz, 1H), 5.17 (d, J=4.8 Hz, 1H), 1.87 (s, 3H), 1.86 (s, 3H).

EXAMPLE 15

(±)-cis-3-Acetyloxy-4-(2-thienyl)azetidin-2-one (Xc)

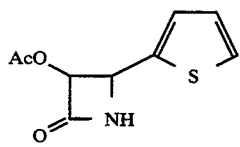

A 70% aqueous solution of acetic acid (0.35 mL glacial acetic acid and 0.15 mL water) was added in one portion to a stirred solution of compound IXc (0.431 g, 1.03 mmol) in dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichloromethane, and then placed on a silica gel column measuring 4" by 0.5". Elution using a gradient of 10 through 60% EtOAc in hexane provided less polar side products and then the title compound (0.154 g, Y: 75%) as a white solid. $^1$H-NMR (CDCl$_3$): δ 7.32 (dd, J=4.7, 1.5 Hz, 1H), 7.03 (m, 2H), 6.75 (bs, 1H), 5.86 (dd, J=4.6, 2.7 Hz, 1H), 5.27 (d, J=5.3 Hz, 1H), 1.83 (s, 3H); $^{13}$C-NMR (CDCl$_3$): δ 169.3, 165.5, 138.4, 127.1, 127.07, 126.2, 78.3, 54.0, 20.0.

EXAMPLE 16

(±)-cis-3-Triethylsilyloxy-4-(2-furyl)-azetidin-2-one (XIIa)

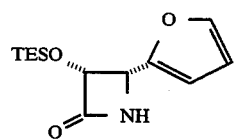

Acetoxy lactam Xb (3.78 g, 19.4 mmol) in 60 mL of methanol was stirred with K$_2$CO$_3$ (20 mg, 0.14 mmol) for 90 min and the solution neutralized with Dowex 50W-X8 and filtered. The filtrate was concentrated and the residue dissolved in 80 mL of anhydrous THF and stirred at 0° C. with imidazole (1.44 g, 21.2 mmol) and TESCl (triethylsilylchloride 3.4 mL, 20.2 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 4.47 g (Y: 86%) of the title compound as a colorless oil; IR(-film) 3276 (broad), 1768, 1184, 732 cm$^{-1}$; $^1$H-NMR (CDCl$_3$, 300 MHz) δ 7.38 (s, 1H), 6.39 (bs, 1H), 6.35 (s, 2H), 5.05 (dd, J=4.6, 2.3 Hz, 1H), 4.78 (d, J=4.6Hz, 1H), 0.82 (t, J=8.5 Hz, 6H), 0.50 (dq, J=8.5, 1.8 Hz, 9H); $^{13}$C-NMR (CDCl$_3$, 75.5 Hz) δ 169.6, 150.4, 142.6, 110.5, 109.1, 79.6, 53.2, 6.4, 4.4; FABMS (DCI) M+H calcd for C$_{13}$H$_{21}$NO$_3$Si: 268, Found: 268.

The racemic mixture obtained in Example 13 may be used as substrate for enzymatic hydrolysis using a lipase such as PS-30 from Pseudomonas sp. (Amano International Co.) to give (3R,4R)-3-hydroxy-4-(2-furyl)azetidin-2-one. The method of enzymatic resolution using the lipase PD-30 and other enzymes is disclosed in our co-pending application U.S. Ser. No. 092,170, filed Jul. 14, 1993 which is hereby incorporated by reference in its entirety. Subsequently, the pertinent part of this example may be followed to convert (3R,4R)-3-hydroxy-4-(2-furyl)azetidin-2-one to (3R, 4R)-3-triethylsilyoxy-4-(2-furyl)azetidine-2-one.

EXAMPLE 17

(±)-cis-3-Triethylsilyloxy-4-(2-furyl)-N-t-butoxycarbonylazetidin-2-one (VIIa)

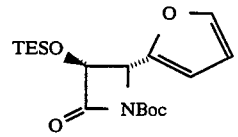

Azetidinone XIIa (2.05 g, 7.7 mmol) in 30 mL of dichloromethane was stirred at 0° C. with diisopropylethyl amine (1.5 mL, 8.6 mmol) and di-t-butyldicarbonate (2.0 g, 9.2 mmol) in addition to a catalytic amount of dimethylaminopyridine (DMAP). The solution was diluted with dichloromethane and washed with brine, dried over MgSO$_4$ and concentrated. The residue was chromatographed over silica gel (eluted with 8:1 hexane/ethyl acetate) to give 2.0 (Y: 70%) of the title compound as a waxy solid; IR(KBr) 1822, 1806, 1712, 1370, 1348, 1016 cm$^{-1}$; $^1$H-NMR (CDCl$_3$, 300 MHz) δ 7.38 (m, 1H), 6.34 (m, 2H), 5.04 (ABq, J=12.4, 5.5 Hz, 2H), 1.39 (s, 9H), 0.82 (t, 9H), 0.50 (m, 6H); $^{13}$C-NMR (CDCl$_3$, 75.5 Hz) δ 165.7, 148.0, 147.7, 142.8, 110.5, 109.7, 83.4, 77.4, 56.0, 27.8, 6.3, 4.4; DCIMS M+H calcd for C$_{18}$H$_{29}$NO$_5$Si: 368, Found: 368.

EXAMPLE 18

(±)-cis-3-Triethylsilyloxy-4-(2-thienyl)-azetidin-2-one (XIIb)

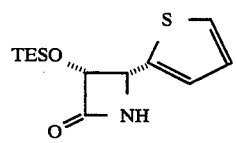

A solution of 3-acetoxy lactam Xc (2.5 g, 11.8 mmol) was dissolved in methanol (10 mL) and treated with saturated aqueous sodium bicarbonate (10 mL) and the resulting slurry was allowed to stir at ambient temperature for 3 h. The reaction was then diluted with ethyl acetate (20 mL) and washed with water (15 mL). The aqueous fraction was back extracted several times with ethyl acetate and the combined organic fractions were dried (MgSO$_4$) and concentrated to give a yellow solid (Y: 1.7 g). The crude material was dissolved in dry tetrahydrofuran (20 mL) and the solution was cooled to 5° C. in an ice/water bath. Imidazole (752 mg, 1.1 eq) was then added. After stirring 5 min, triethylchlorosilane (1.85 mL, 1.1 eq) was added dropwise. The resulting suspension was allowed to stir for 3 h at that temperature; then the solids were removed by filtration. The organic fraction was washed with water (2×20 mL) then dried (MgSO$_4$) and concentrated. The crude product was purified by silica gel column chromatography (eluted with hexanes/ethyl acetate 7:3) to give the desired product as a colorless solid (1.5 g, Y: 45%). m.p. 70°-71° C.; $^1$H-NMR (300 MHz, CDCl$_3$): δ 7.32-7.30 (m, 1H); 7.05-6.98 (m, 2H), 5.06-5.05 (m, 2H), 0.82 (t, 9H, J=8 Hz), 0.55-0.46 (m, 6H); $^{13}$C-NMR (75.6 MHz, CDCl$_3$): δ 169.1, 139.7, 126.5, 126.4, 125.8, 79.4, 55.1, 6.3, 4.4.

Alternate Run:

Acetoxy lactam Xc (2.0 g, 9.37 mmol) in 40 mL of methanol was stirred with K$_2$CO$_3$ (60 mg, 0.43 mmol) for 30 min and the solution neutralized with Dowex 50W-X8 and filtered. The filtrate was concentrated and the residue dissolved in 50 mL of anhydrous THF and stirred at 0° C. with imidazole (0.85 g, 11.3 mmol) and TESCl (1.9 mL, 12.5 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 2.13g (Y: 86%) of the title product as a colorless oil.

EXAMPLE 19

(±)-cis-3-Triethylsilyloxy-4-(2-thienyl)-N-t-butoxycarbonylazetidin-2-one (VIIb)

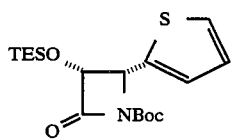

A solution of the silyl azetidinone XIIb (425.7 mg, 1.48 mmol) was dissolved in dichloromethane (10 mL) and cooled to 5° C. in an ice/water bath. The reaction was treated with a catalytic amount of DMAP then di-t-butyldicarbonate (388.4 mg, 1.2 eq). After stirring 2 h at that temperature the reaction was quenched with saturated aqueous sodium bicarbonate (5 mL) and the organic fraction was washed with water (5 mL) then dried (MgSO$_4$), passed through a short plug of silica gel and concentrated to give the desired product as a colorless oil (525.3 mg, Y: 93%); $^1$H-NMR (300 MHz, CDCl$_3$): δ 7.31-7.29 (m, 1H), 7.08-7.07 (m 1H), 7.00-6.58 (m, 1H), 5.31 (d, 1H, J=6 Hz), 5.03 (d, 1H, J=6 Hz), 1.40 (s, 9H), 0.83 (t, 9H, J=8 Hz), 0.56-0.47 (m, 6H); $^{13}$C-NMR (75.6 MHz, CDCl$_3$): δ 165.5, 147.5, 136.4, 127.6, 126.2, 126.1, 83.3, 77.3, 57.9, 27.7, 6.2, 4.3.

EXAMPLES 20-24

(±)-cis-3-Triethylsilyloxy-4-isobutenyl-N-t-butoxycarbonylazetidin-2-one (VIIc) can be made by the reaction sequence of Scheme III.

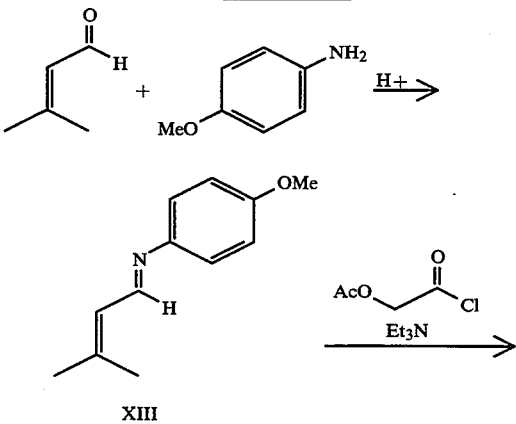

SCHEME III

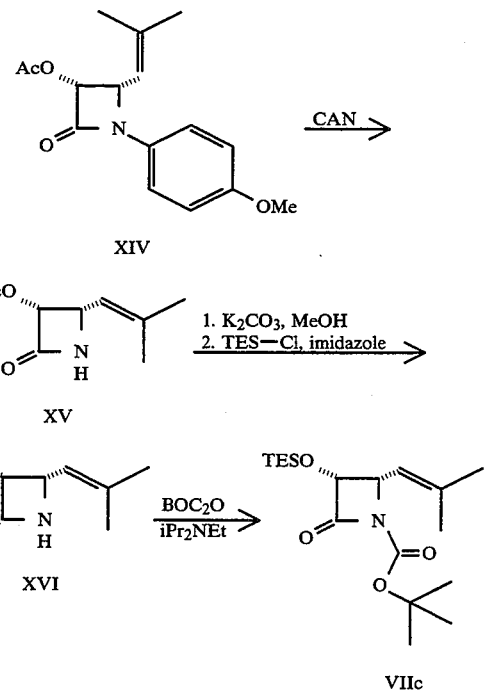

-continued
SCHEME III

EXAMPLE 20

N-4-methoxy-N-(3-methyl-2-butenyl)benzenamine (XIII)

A solution of p-anisidine (5.7 g, 46.3 mmol) was dissolved in diethylether (100 mL) and was treated with a catalytic amount of p-toluensulfonic acid (10 mg). To this was added 3-methyl-2-butenal (2.67 mL, 50.9 mmol) in one portion and the reaction was allowed to stir at ambient temperature for 16 h. The solvent was then evaporated on a rotary evaporator at 0.5 torr to furnish the desired imine (8.7 g, 100%) as a brown oil; $^1$H NMR 300 MHz, CDCl$_3$): δ 8.38 (d, 1H, J=9.5 Hz), 7.11 (dd, 2H, J=2.2, 6.7 Hz), 6.88 (dd, 2H, J=2.2, 6.7 Hz), 6.22-6.18 (m, 1H), 3.81 (s, 3H), 2.01 (s, 3H), 1.95 (s, 3H).

EXAMPLE 21

(±)-cis-N-(4-methoxyphenyl)-3-acetyloxy-4-isobutenylazetidin-2-one (XIV)

A solution of acetoxyacetyl chloride (6.9 g, 50.5 mmol) was dissolved in ethyl acetate (100 mL) and cooled to −30° C. under an inert atmosphere. To this solution was added triethylamine (7.0 mL, 50.5 mmol) over a 5 min period. The resulting white slurry was then treated with an ethyl acetate solution of imine XIII (8.7 g, 40 mL) dropwise over a 20 min period. The resulting green-brown slurry was then gradually allowed to warm to ambient temperature over a 4 h period. The slurry was then filtered through a pad of celite and the filtrate was washed with water then brine. The organic fraction was dried (MgSO$_4$) and concentrated to give a brown oil. The crude product was purified by careful silica gel chromatography (eluted with hexanes/ethyl acetate 8:2) to furnish an orange oil which solidified on standing. This was recrystallized from dichloromethane/hexanes to furnish the desired product as a pale yellow solid (4.4 g, 32%); $^1$H NMR (300 MHz, CDCl$_3$):

δ 7.32 (d, 2H, J=9.1 Hz), 6.86 (d, 2H, J=9.1 Hz), 5.59 (dd, 1H, J=3.0, 7.8 Hz), 5.14-5.10 (m, 1H), 4.96 (dd, 1H, J=4.8, 9.3 Hz), 3.77 (s, 3H), 2.11 (s, 3H, ), 1.81 (s, 3H), 1.78 (s, 3H).

EXAMPLE 22

(±)-cis-3-Acetyloxy-4-isobutenylazetidin-2-one (XV)

A solution of the N-aryl lactam XIV (4.88 g, 16.2 mmol) was dissolved in acetonitrile (50 mL) and cooled to 0°-5° C. in an ice bath. To this was added a cold solution of ceric ammonium nitrate (26.6 g, 48.6 mmol, 50 mL) in one portion. The deep red reaction was allowed to stir for 10 min and during that time the color gradually lightened to orange. The cold solution was transferred to a separatory funnel, diluted with water, and extracted with ethyl acetate. The organic fraction was washed with several portions of 10% aqueous sodium sulfite, followed by saturated aqueous sodium bicarbonate. The organic fraction was dried (MgSO$_4$) and concentrated to give the desired product (2.71 g, 91%) as a yellow-orange solid that was used directly in the next step; $^1$H NMR (300 MHz, CDCl$_3$): δ 6.11 (bs, 1H), 5.73 (dd, 1H, J=2.2, 4.7 Hz), 5.12-5.08 (m, 1H), 4.63 (dd, 1H, 4.7, 9.1 Hz), 2.09 (s, 3H), 1.75 (s, 3H), 1.67 (s, 3H).

EXAMPLE 23

(±)-cis-3-Triethylsilyloxy-4-isobutenylazetidin-2-one (XVI)

Acetoxy lactam XV (1.47 g, 8.0 mmol) was dissolved in methanol (15 mL) and was stirred with K$_2$CO$_3$ (110.5 mg, 0.8 mmol) for 3h at ambient temperature. The solution was then neutralized with Dowex 50W-X8 resin and then filtered. The filtrate was concentrated and the crude solid was dissolved in THF (25 mL) and cooled to 5° C. in an ice bath. Imidazole (544.0 mg, 8.0 mmol) was added and once dissolved, triethylsilyl chloride (1.34 mL, 8.0 mmol) was added dropwise via syringe. The resulting slurry was allowed to warm to ambient temperature and stir overnight. The solution was filtered and the filtrate was washed with water, then brine. The organic fraction was dried (MgSO$_4$) and concentrated. The crude solid was purified by silica gel chromatography (eluted with hexanes/ethyl acetate 3:1) to furnish the desired product (612 mg, 30%) as a pale yellow solid; $^1$H NMR (300 MHz, CDCl$_3$): δ 5.87 (bs, 1H), 5.31-5.26 (m, 1H), 4.90 (dd, 1H, J=2.2, 4.7 Hz), 4.42 (dd, 1H, J=4.7, 9.3 Hz), 1.74 (s, 3H), 1.28 (s, 3H), 0.98-0.91 (m, 9H), 0.71-0.55 (m, 6H).

EXAMPLE 24

(±)-cis-3-Triethylsilyloxy-4-isobutenyl-N-t-butoxycarbonyl-azetidin-2-one (VIIc)

Azetidinone XVI (1.01 g, 3.95 mmol) was dissolved in dichloromethane (20 mL) and was treated with diisopropylethylamine (0.68 mL, 3.95 mmol) and a catalytic amount of dimethylaminopyridine. To this solution was added di-t-butyldicarbonate (1.02 g, 4.68 mmol) and the solution was allowed to stir for 24 h at ambient temperature. The solution was then diluted with additional dichloromethane and washed with water then brine. The organic fraction was dried (MgSO$_4$) and concentrated. The residue was purified by silica gel chromatography (eluted with hexanes/ethyl acetate 8:2) to give the desired product (1.26 g, 90%) as a colorless oil; $^1$H NMR (300 MHz, CDCl$_3$): δ 5.24 (d, 1H, J=9.6 Hz), 4.86 (d, 1H, J=5.7 Hz), 4.72 (dd, 1H, J=6.0, 9.9 Hz), 1.78 (d, 3H, J=1.1 Hz), 1.75 (d, 3H, J=1.1 Hz), 1.47 (s, 9H), 0.96-0.91 (m, 9H), 0.64-0.55 (m, 6H).

In Vitro Cytotoxicity Data

Compounds of the present invention showed in vitro cytoxicity activity against human colon carcinoma cells HCT-116 and HCT-116/VM46. The HCT-116/VM46 cells are cells that have been previously selected for teniposide resistance and express the multi-drug resistance phenotype, including resistance to paclitaxel. Cytotoxicity was assessed in HCT-116 human colon carcinoma cells by XTT (2,3-bis(2-methoxy-4-nitro-5-sulfphenyl)-5-[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines," Cancer Res. 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an IC$_{50}$, which is the drug concentration required to inhibit cell proliferation (i.e., absorbance at 450 nm) to 50% of that of untreated control cells. The IC$_{50}$ values for compounds evaluated in this assay are given in Table I.

TABLE I

| In vitro cytotoxicity data against human colon carcinoma cells. | | |
|---|---|---|
| COMPOUND | IC$_{50}$HCT116 (nM) | IC$_{50}$HCT116/ VM46 (nM) |
| paclitaxel | 1.3–3.5 | 244–403 |
| Ia | 1.2 | 30.5 |
| Ib | 1.3–3.0 | 2.8–13.9 |
| Ic | 0.6 | 12.3 |
| Id | 1.3 | 3.3 |

The compounds of the instant invention have tumor inhibiting activities in mammals. Thus, another aspect of the instant invention concerns with a method for inhibiting mammalian tumors sensitive to a compound of formula I.

The present invention also provides pharmaceutical formulations (compositions) containing a compound of formula I in combination with one or more pharmaceutically acceptable, inert or physiologically active, carriers, excipients, diluents or adjuvants. Examples of formulating paclitaxel or its related derivatives (including a possible dosage) are described in numerous literatures, for example in U.S. Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The compounds of present invention can be used as paclitaxel for treating mammalian tumors. The mode, dosage and schedule of administration of paclitaxel in human cancer patients have been extensively studied. See, for example *Ann. Int. Med.*, 111, pp 273–279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50–275 mg/m² of the patient. An oncologist skilled in the art of cancer treatment will be able to ascertain, without undue experimentation, appropriate protocols for effective administration of the compounds of this present invention such as by referring to the earlier studies of paclitaxel and its derivatives.

I claim:

1. A compound of formula I

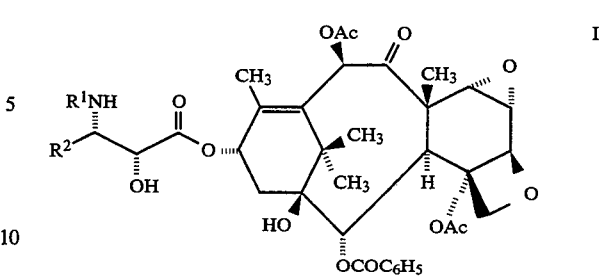

in which $R^1$ is —$COR^z$, in which $R^z$ is $RR^oN$—, $RHN$—, $RO$— or $R$;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

2. A compound of claim 1 in which is RO— or R; $R^2$ is $C_{2-6}$ alkenyl, phenyl, furyl or thienyl; and R is $C_{1-6}$ alkyl or phenyl.

3. The compound of claim 2 that is 6,7-α-epoxypaclitaxel.

4. The compound of claim 2 that is 3'-N-debenzoyl-N-t-butoxycarbonyl-3'-desphenyl-3'-(2-furyl)-6,7-α-epoxypaclitaxel.

5. The compound of claim 2 that is 3'-desphenyl-3'-(2-furyl)-6,7-α-epoxypaclitaxel.

6. The compound of claim 2 that is 3'-N-debenzoyl-N-t-butoxycarbonyl-3'-desphenyl-3'-isobutenyl-6,7-α-epoxypaclitaxel.

7. A pharmaceutical formulation which comprises as an active ingredient a compound as claimed in any one of claims 1 to 6, or a pharmaceutically acceptable salt thereof, associated with one or more pharmaceutically acceptable carriers, excipients or diluents therefor.

8. A method for treating mammalian tumors which comprises administering to a mammal a tumor sensitive amount of a compound as claimed in any one of claims 1 to 6.

9. 6,7-α-Epoxy Baccatin III of the formula

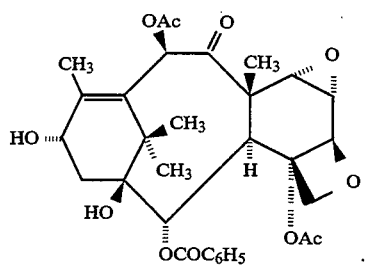

* * * * *